(12) United States Patent
Schneider et al.

(10) Patent No.: US 10,295,451 B2
(45) Date of Patent: May 21, 2019

(54) HOLOGRAPHIC DEVICE AND OBJECT SORTING SYSTEM

(71) Applicants: IMEC VZW, Leuven (BE); Universiteit Gent, Ghent (BE)

(72) Inventors: Bendix Schneider, Leuven (BE); Peter Bienstman, Ghent (BE); Joni Dambre, Gavere (BE); Geert Vanmeerbeeck, Keerbergen (BE); Liesbet Lagae, Leuven (BE)

(73) Assignees: IMEC VZW, Leuven (BE); UNIVERSITEIT GENT, Ghent (BE)

( * ) Notice: Subject to any disclaimer, the term of this patent is extended or adjusted under 35 U.S.C. 154(b) by 0 days.

(21) Appl. No.: 15/738,227

(22) PCT Filed: Jun. 28, 2016

(86) PCT No.: PCT/EP2016/065068
§ 371 (c)(1),
(2) Date: Dec. 20, 2017

(87) PCT Pub. No.: WO2017/001438
PCT Pub. Date: Jan. 5, 2017

(65) Prior Publication Data
US 2018/0195945 A1    Jul. 12, 2018

(30) Foreign Application Priority Data

Jun. 30, 2015 (EP) ..................... 15174589

(51) Int. Cl.
*G01N 15/02* (2006.01)
*G03H 1/02* (2006.01)
(Continued)

(52) U.S. Cl.
CPC ....... *G01N 15/0227* (2013.01); *G01N 15/147* (2013.01); *G01N 15/1434* (2013.01);
(Continued)

(58) Field of Classification Search
CPC ...................... G01N 15/0227; G01N 15/1434
See application file for complete search history.

(56) References Cited

U.S. PATENT DOCUMENTS

| | | | |
|---|---|---|---|
| 2005/0248761 A1 | 11/2005 | Nieuwenhuis et al. | |
| 2012/0148141 A1* | 6/2012 | Ozcan | G06K 9/0014 382/133 |
| 2017/0241891 A1* | 8/2017 | Grier | G01N 15/0227 |

FOREIGN PATENT DOCUMENTS

| | | |
|---|---|---|
| EP | 2 602 608 A1 | 6/2013 |
| EP | 2 602 608 B1 | 9/2016 |

OTHER PUBLICATIONS

Yevick, Aaron et al., "Machine-Learning Approach to Holographic Particle Characterization", Optics Express, vol. 22, No. 22, Oct. 22, 2014, pp. 26884-26890.*
(Continued)

*Primary Examiner* — Roy M Punnoose
(74) *Attorney, Agent, or Firm* — McDonnell Boehnen Hulbert & Berghoff LLP (57) ABSTRACT

A device for extracting at least one object characteristic of an object (106) is presented, the device comprising: a light sensor (101) for recording a hologram of an object and a processing unit (102) coupled to the light sensor and configured for extracting at least one object characteristic from the hologram; wherein the processing unit is configured for extracting the at least one object characteristic from a section of the hologram without reconstructing an image representation of the object. Further, a device (200) for sorting an object (106), a method for identifying an object and a method for sorting objects is presented.

14 Claims, 8 Drawing Sheets

(51) Int. Cl.
*G03H 1/04* (2006.01)
*G01N 15/14* (2006.01)
*G01N 15/00* (2006.01)

(52) U.S. Cl.
CPC ............ *G03H 1/02* (2013.01); *G03H 1/0443* (2013.01); *G01N 2015/008* (2013.01); *G01N 2015/0073* (2013.01); *G01N 2015/0233* (2013.01); *G01N 2015/149* (2013.01); *G01N 2015/1454* (2013.01); *G01N 2015/1493* (2013.01); *G03H 2001/0447* (2013.01); *G03H 2226/02* (2013.01); *G03H 2226/11* (2013.01)

(56) References Cited

OTHER PUBLICATIONS

PCT International Search Report and Written Opinion, PCT International Application No. PCT/EP2016/065068, dated Sep. 14, 2016, 18 pages.

Vercruysse, Dries et al., "Three-Part Differential of Unlabeled Leukocytes With a Compact Lens-Free Imaging Flow Cytometer", Lab on a Chip, vol. 15, No. 4, Jan. 1, 2015, pp. 1123-1132.

Schneider, B. et al., "Using Neural Networks for High-Speed Blood Cell Classification in a Holographic-Microscopy Flow-Cytometry System", Progress in Biomedical Optics and Imaging, SPIE—International Society for Optical Engineering, vol. 9328, Mar. 2, 2015, pp. 93281F-1-93281F-4.

Vandoorne, K., et al., "Experimental Demonstration of Reservoir Computing on a Silicon Photonics Chip", Nature Communications, Mar. 2014, vol. 5(3541), pp. 1-6, DOI:10.1038/ncomms4541.

* cited by examiner

HOLOGRAPHIC DEVICE AND OBJECT SORTING SYSTEM

The present application is a section 371 U.S. patent application claiming priority to PCT/EP2016/065068, filed Jun. 28, 2016, which claims priority from EP Application No. 15174589.0, filed Jun. 30, 2015, the contents of which are hereby incorporated by reference.

FIELD OF THE INVENTION

The invention relates to devices and techniques for particle characterization. In particular, the invention relates to lens-free devices. More in particular, the invention relates to fluidic devices for in flow particle characterization.

BACKGROUND TO THE INVENTION

In digital holographic microscopy, light wave front information from an illuminated object is digitally recorded as a hologram. By reconstructing an image representation of the object from the hologram, characteristics of the object can be extracted from that image representation. However, such reconstruction relates to a high computational cost that limits the speed of the object characterization.

Extracting particle and distributions characteristics from holograms, bright field images, or Fraunhofer diffraction patterns has already been studied in the past and is generally solved by applying different numerical algorithms involving inversion, nonlinear pattern matching, or performing image analysis decomposition. Since integrals of special functions or an extensive use of Fast Fourier Transformation intervene in most of these algorithms, they all suffer from a tremendous increase in computational cost when they have to be performed at high speed. This severely limits real-time particle characterization in high-throughput applications.

SUMMARY OF THE INVENTION

It is an object of the invention to provide a device and a method that allows fast and accurate characterization of objects at low computational cost.

The above objective is accomplished by a method and device according to the present invention. In a first aspect of the invention, a device for extracting at least one object characteristic of an object is presented, comprising: a light sensor configured for recording a hologram of an object; and a processing unit coupled to the light sensor, the processing unit being configured for extracting at least one object characteristic from the hologram; wherein the processing unit is configured for extracting the at least one object characteristic from only a section of the hologram without reconstructing an image representation of the object.

According to an embodiment of the invention, the light sensor is configured for recording only the section of the hologram used for extracting the at least one object characteristic.

According to an embodiment of the invention, the light sensor consists of a single row of light recording elements for recording the section of the hologram.

According to an embodiment of the invention, the light sensor consists of two rows of light recording elements intersecting each other thereby forming a cross-shape.

According to an embodiment of the invention, the processing unit comprises a machine learning component, such as for example an artificial neural network, calibrated for extracting the at least one object characteristic.

According to an embodiment of the invention, the processing unit comprises a support vector machine calibrated for extracting the at least one object characteristic.

According to an embodiment of the invention, recording the hologram and extracting the at least one object characteristic comprises receiving light of the hologram and determining the at least one object characteristic using the directly received light without converting the light into electrical signals.

According to an embodiment of the invention, the light sensor is configured to record intensity and phase of light of the hologram. The processing unit is then configured to extract the at least one object characteristic using the recorded intensity and phase.

According to an embodiment of the invention, the light sensor comprises optical coupling elements for recording the hologram, e.g. grating couplers.

According to an embodiment of the invention, the at least one object characteristic comprises the object size and/or the object type and/or the object internal structure and/or the object homogeneity.

According to an embodiment of the invention, the object is a biological cell.

According to an embodiment of the invention, the at least one object characteristic comprises a size of the cell and/or a size of a nucleus of the cell and/or the cell type and/or the cell internal structure and/or the cell homogeneity.

According to an embodiment of the invention, the object is a Red Blood Cell or a White Blood Cell or a Circulating Tumor Cell.

According to an embodiment of the invention, the processing unit is a photonic integrated circuit. According to an embodiment of the invention, the processing unit consists of photonic components.

According to an embodiment of the invention, the device further comprises a fluidic channel, e.g. a micro-fluidic channel. In such an embodiment, the light sensor is positioned such that holograms of illuminated objects in the fluidic channel can be recorded or captured by the light sensor.

In a second aspect of the invention, an in-flow object sorting system is presented, comprising: at least one fluidic channel for propagating a fluid sample comprising at least one object; a coherent light source associated with each fluidic channel, positioned to illuminate objects propagating in that fluidic channel; a device as described in the first aspect or any of its embodiments, the device being associated with each fluidic channel and positioned to record or capture a hologram of an illuminated object in that fluidic channel; and a sorter associated with each fluidic channel, the sorter being coupled to the device and positioned downstream of the device, and wherein the sorter is configured for sorting the illuminated objects in the associated fluidic channel based on the extracted at least one object characteristic.

In a third aspect of the invention, a method for extracting at least one object characteristic of an object is presented, comprising: providing a fluid sample comprising at least one object; illuminating the at least one object; recording a hologram of the illuminated at least one objects; extracting at least one characteristic from the at least one object from the recorded hologram; wherein the extraction of the at least one characteristic of the object is performed using only a section of the recorded hologram, without reconstructing an image representation of the at least one object.

According to an embodiment of the invention, the recording of the holograms comprises recording intensity and phase of light representing the holograms and the extraction of the at least one characteristic of the at least one object is done using the recorded intensity and phase.

In a fourth aspect of the invention, a method for sorting objects in-flow is presented, comprising the method for extracting at least one object characteristic of at least one object as described above; and further comprising sorting each object based on the extracted at least one characteristic of that object.

It is an advantage of embodiments of the invention to provide a device which can identify objects with high accuracy at low computational complexity.

It is an advantage of embodiments of the invention to provide a system which allows real-time classification of cells at high speed, e.g. 100000 to 1 million objects per second.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiments) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Throughout the description reference is made to "fluid sample". "Fluid sample" may refer to any body fluid that can be isolated from the body of an individual. Such a body fluid may refer to, but not limited to, blood, plasma, serum, bile, saliva, urine, tears, perspiration. Fluid sample may also refer to any fluid, e.g. a saline solution, suitable for transporting objects or components in a fluidic or micro-fluidic system. Objects may refer to any of the components contained in, for example, blood, plasma, serum, bile, saliva, urine, tears, perspiration.

Throughout the description reference is made to a "light sensor". This may refer to any electrical or optical component suitable for recording or capturing light signals. For example, an image sensor or a photonic component or circuit, e.g. a grating coupler.

Throughout the description reference is made to a "hologram". This refers to an interference pattern of an object illuminated by a coherent light source, traditionally producing coherent light. Such an interference pattern is formed by the interference of scattered light from the object and the original light from the coherent light source.

Where in embodiments of the present invention reference is made to "part of a hologram" reference is made to not all of a hologram. "Part of a hologram" also encompasses less than 90% of a hologram, e.g. less than 75% of a hologram, e.g. less than 50% of a hologram, e.g. less than 30% of a hologram.

The problem of high computational cost as described above in the background section is solved by using only a part of the information of a recorded hologram of an object. It is observed by the inventors that object characteristics can still be extracted from the hologram when parts of the hologram information is discarded. By using only a part of the hologram information and not performing a reconstruction of the object from the full hologram, computational cost can be drastically reduced.

Different aspects of the invention are described in the following paragraphs.

In a first aspect of the invention, a device is presented. The device may be a completely integrated device, e.g. a chip. The device can be used to extract object characteristics of objects. These object characteristics may be at least, but not limited to, one of the following characteristics: object type, object size, object internal structure, or object homogeneity. In particular if the object is a biological cell, these object characteristics may be cell type, cell size, cell internal structure, or cell homogeneity. The device comprises a light sensor for recording a hologram of an object. This light sensor comprises a sensing side which is suitable for capturing or recording an interference pattern (=hologram) of an object that is illuminated by a coherent light source. For example, when an object located above the sensing side is illuminated, the interference pattern formed by the interference of scattered light from the object and the original light from the coherent light source can be captured or recorded by this sensing side. The device further comprises a processing unit that is coupled to the light sensor such that captured or recorded holograms can be received by the processing unit. The processing unit is configured to extract characteristics from an illuminated object by using only a section of the recorded hologram.

Figure 1:
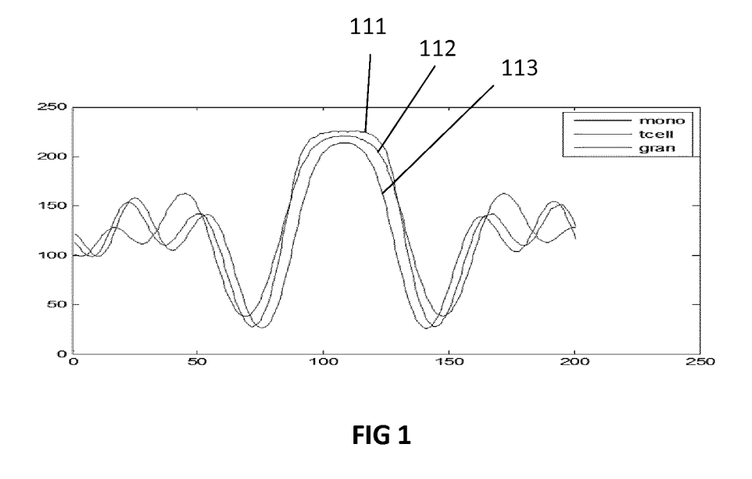
FIG. 1 illustrates identification of cells

It is known in the art of holograms that when splitting a hologram in half, the whole scene can still be seen in each part of the hologram because each point on a holographic recording includes information about light scattered from every point in the scene. It was observed by the inventors that object characteristics can still be extracted from a part of the hologram information. The graph in FIG. 1 represents the results of an experiment. FIG. 1 shows that different types of cells (monocytes 111, t-cells 112, granulocytes 113) can still be identified using a part of the information of the hologram of the cell, in this case only a one-dimensional radial slice. It is an advantage of the invention that less information needs to be processed thereby leading to a reduction of the computational cost. The data in FIG. 1 was obtained by extracting or selecting a 1D radial slice out of every 2D image of a data set. The 1D radial slice represents a single line of light recording elements of a light sensor.

According to an embodiment of the invention, the location of the slice is aligned with the centre of the object when capturing or recording light. Thus, when capturing a hologram of an object, the slice is positioned such that the centre of the hologram is aligned with the slice. The selection of the width of the slice depends on the computational cost which can be afforded by the user while still achieving appropriate speeds for object characterization. For example, the width may be below 50 um, e.g. 40 um, 30 um, 20 um, 10 um, 5 um or below. In a particular experiment the inventors discovered that object characterization can be done with a slice of pixels, wherein each pixel has a size of 16 um by 16 um. By performing a simple trial and error experiment, the appropriate width of the slice can be determined. During such an experiment, the computational cost related to the width of the slice can then be determined.

Figure 2:
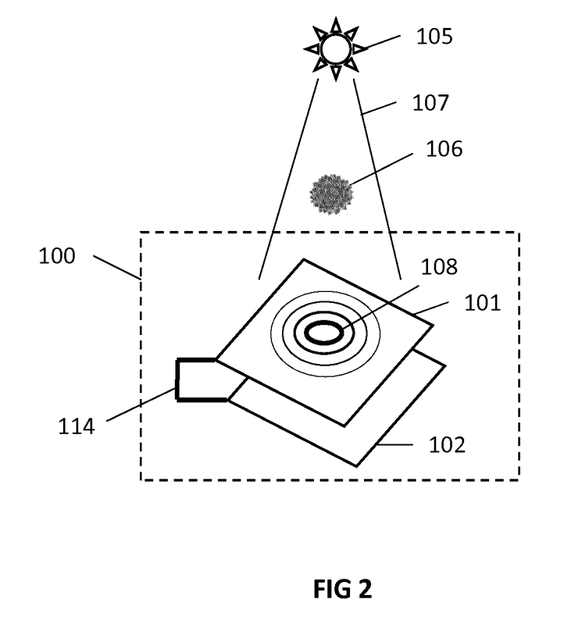
FIG. 2 illustrates a device according to an embodiment of the present invention.

An embodiment of the invention is featured in the setup illustrated in FIG. 2. The setup comprises a coherent light source 105, an object 106 and a device 100. The coherent light source 105 is positioned such that the light wavefront 107 generated by the coherent light source 105 illuminates the object 106. The light sensor 101 is positioned such that a hologram 108 of the illuminated object can be recorded by the light sensor 101. A processing unit 102 is coupled 114 to the light sensor 101 and performs the processing only on a section of the recorded hologram 108. Alternatively, a means for creating coherent light from the coherent light source 105 may be used, e.g. a structure with one or more pinholes. The use of such a means applies to all embodiments disclosed in this description.

According to an embodiment of the invention, and as illustrated in FIG. 2, the light sensor records a complete hologram of the object. This hologram is transferred to the processing unit. The processing unit extracts a section of the hologram. This extraction may comprise a simple image processing step. This image processing step may be performed by the processing unit. The rest of the hologram information is discarded. Only the extracted section of the hologram is used by the processing unit to extract object characteristics.

According to another embodiment of the invention, the light sensor is configured to record only a section of the hologram, for example only a line scan or a 1D line scan. This section is then transferred to the processing unit. For example, only a part of the area of the sensing side of the light sensor is active. This active area is then used to record a section of the hologram. For example, a conventional image sensor may be used of which only a part of the sensing side, e.g. a single row of pixels, is active. It is an advantage of the invention that by recording only a section of the hologram, power consumption of the device can be reduced. In a massively parallelized system comprising a plurality of devices, this reduction of power consumption is an important advantage. According to an embodiment of the invention, the geometry of the light sensor is adapted to the geometry of the section of the hologram that is needed for processing. Hence, the size of the light sensor is smaller than the size of the complete hologram of the object. In other words, the geometry of the light sensor corresponds to the geometry of the section of the hologram that is required for identification.

According to a particular embodiment of the invention, the light sensor consists of two, three or four rows of light recording elements for recording the section of the hologram.

According to a particular embodiment of the invention, the light sensor consists of a single row of light recording elements for recording the section of the hologram. The single row of light recording elements are positioned such that a slice of the hologram can be recorded. For example, the row is positioned such that the center of the object can be imaged. The single row of light recording elements may be a 1D radial slice. This is a slice of which the orientation is perpendicular to the propagation path of an object. The single row of light recording elements may also be a 1D axial slice. This is a slice of which the orientation is substantially parallel to the propagation path of an object.

Figure 3A:
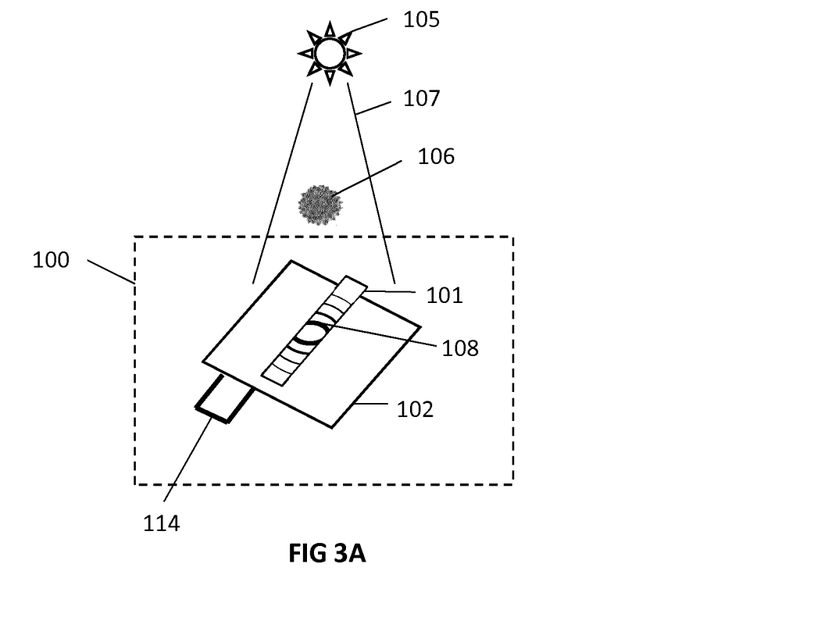
FIG. 3A illustrates a device according to an embodiment of the present invention.

An embodiment of the invention is featured in the setup illustrated in FIG. 3A. Certain parts of this setup are similar to the described setup of FIG. 2. However, in this setup, the light sensor 101 is sized such that only a section of the hologram 108 is recorded. According to a particular embodiment of the invention, the geometry of the light sensor 101 corresponds to a slice of the hologram 108 of the object 106. Thus, instead of recording a 2D image, the light sensor 101 only records a 1D slice, e.g. a 1D radial slice, of the hologram 108.

According to an embodiment of the invention, the light sensor consists of two rows of light recording elements intersecting each other thereby forming a cross-shape. The two rows may be positioned perpendicular to each other. Thus, in a specific embodiment, a radial 1D slice may be combined with a 1D axial slice to further improve the extraction of object characteristics while still reducing the holographic data set. The combination of the 1D radial slice and the 1D axial slice also simplifies the detection of the object. For example, it allows for compensating misalignment of objects. This may be advantageous in fluidic channels in which objects are propagating along a trajectory path. Objects that are not aligned with the defined trajectory path can still be detected and imaged whilst reducing the holographic data set.

Figure 3B:
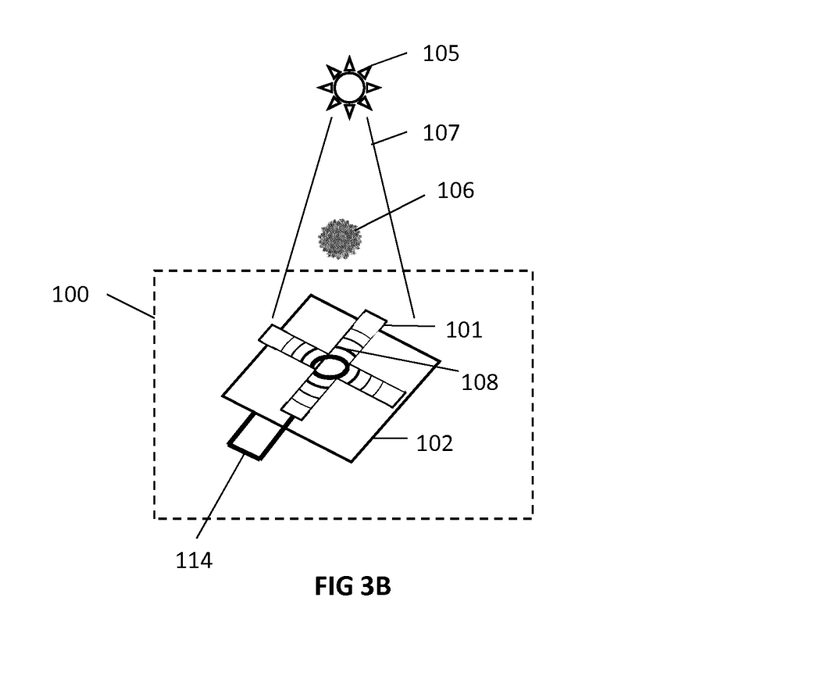
FIG. 3B illustrates an device according to an embodiment of the present invention.

An embodiment of the invention is featured in the setup illustrated in FIG. 3B. Certain parts of this setup are similar to the described setup of FIG. 2. However, in this setup the light sensor 101 is a combination of a 1D radial slice and a 1D axial slice. The light sensor 101 has a cross-shape. Instead of recording a 2D image, the light sensor 101 records a radial 1D slice and an axial 1D slice of the hologram 108. The combined holographic information is then transferred to the processing unit 102.

Figure 3C:
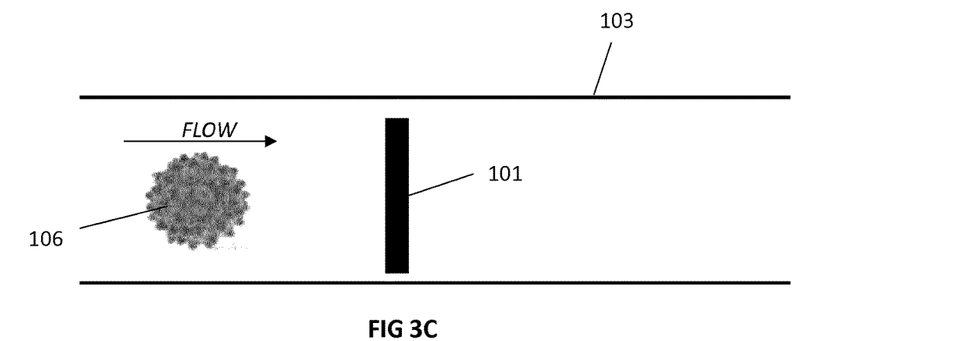
FIG. 3C illustrates a fluidic channel comprising a device according to an embodiment of the present invention.

FIG. 3C illustrates a fluidic channel 103 comprising a light sensor 101. The light sensor 101 is a radial 1D slice. The orientation of the slice is substantially perpendicular to the orientation of the fluidic channel 103 or substantially perpendicular to the direction of the propagation path of the object 106 in the fluidic channel 103.

Figure 3D:
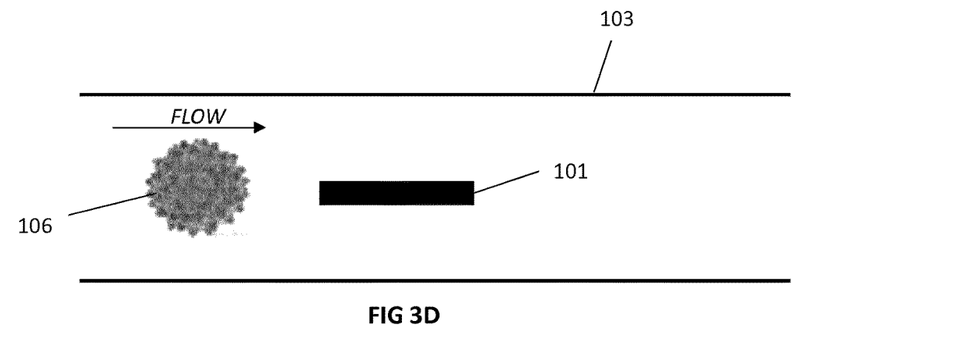
FIG. 3D illustrates a fluidic channel comprising a device according to an embodiment of the present invention.

FIG. 3D illustrates a fluidic channel 103 comprising a light sensor 101. The light sensor 101 is an axial 1D slice. The orientation of the slice is substantially parallel to the orientation of the fluidic channel 103 or substantially parallel to the direction of the propagation path of the object 106 in the fluidic channel 103.

Figure 3E:
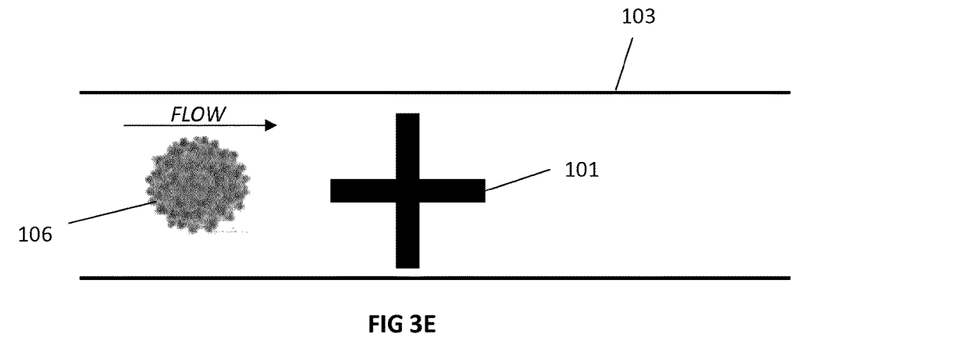
FIG. 3E illustrates a fluidic channel comprising a device according to an embodiment of the present invention.

FIG. 3E illustrates a fluidic channel 103 comprising a light sensor 101. The light sensor 101 is an axial 1D slice combined with a radial 1D slice.

According to an embodiment of the invention, the light recording elements may be elements which convert an optical signal into an electrical signal such as e.g. pixels of an image sensor. In such a case, the light sensor is electrically coupled, e.g. electrically wired or bonded, to the processing unit. The light sensor may be a conventional image sensor such as a CMOS imager.

According to another embodiment of the invention, the light recording elements may be optical in-coupling elements which pick up or capture the light of the hologram. These elements may be grating couplers which couple light into, for example, an optical waveguide. Such optical elements may have, for example, a 10 um by 10 um geometry. These optical in-coupling elements do not convert the light into an electrical signal. No conversion is performed at all. The optical elements merely function as devices that redirect the light into, for example, an optical waveguide. These optical in-coupling elements may be nano- or microstructures patterned on a substrate. They are designed such that light falling on these structures is directed to, for example, an optical waveguide also present on the substrate. As an advantage, no optical information, such as e.g. phase information, of the hologram is lost. In such an embodiment, the light sensor is optically coupled to the processing unit. Thus, light received by the optical coupling elements is redirected or directly transferred to the processing unit. The processing may be a photonic integrated circuit that receives the picked-up light signals as input. The optical coupling between the light sensor and the processing unit may be implemented by one or more optical waveguides. Thus, according to this embodiment of the invention, recording the hologram and extracting the at least one object characteristic comprises: 1) receiving the light of the hologram, and 2) determining at least one object characteristic from the directly received light without converting the light into electrical signals beforehand.

Figure 4:
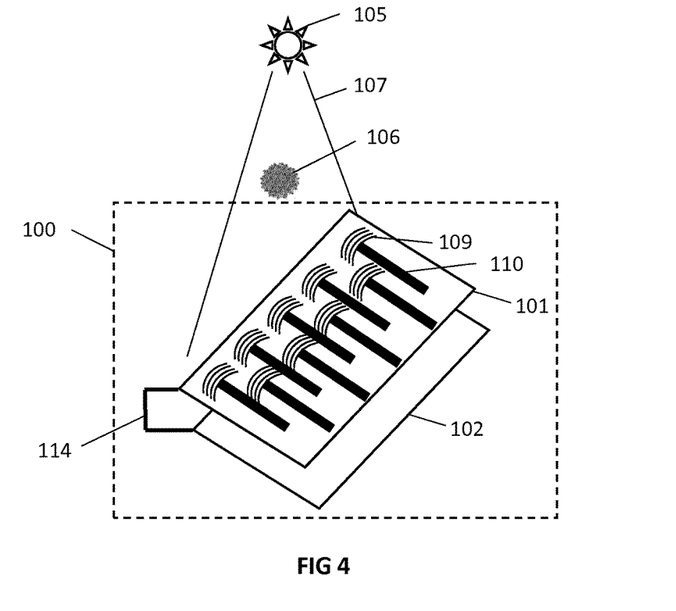
FIG. 4 illustrates a device according to an embodiment of the present invention.

An embodiment of the invention is featured in the setup illustrated in FIG. 4. FIG. 4 illustrates a setup having similar parts as illustrated in FIG. 2. The sensing side of the light sensor 101 comprises optical in-coupling elements 109 for capturing light. The optical coupling elements 109 are optically coupled to optical waveguides 110. The optical waveguides 110 are optically coupled 114 to the processing unit 102 and deliver the light of the hologram to the processing unit 102.

According to an embodiment of the invention, the light sensor is configured to capture or record intensity and phase information of the light of the hologram. The processing unit is then configured to extract object characteristics from the captured or recorded intensity and phase information. It is an advantage that apart from intensity also the phase of the light of the holograms is captured or recorded. By extracting object characteristics from intensity and phase, the extraction is improved, leading to more sensitive and accurate characterization of the objects under test. The simultaneous recording of intensity and phase information can be performed by picking up the light signals, e.g. using optical coupling elements as described above, and directly transferring the light signals to the processing unit. The intensity and phase information is then transferred to the processing unit for the extraction of object characteristics.

According to an embodiment of the invention the processing unit comprises a machine learning component that is calibrated or trained for extracting the at least one object characteristic. The machine learning may comprise an artificial neural network (ANN) or a support vector machine but also any other machine learning technique such as decision tree learning, association rule learning, deep learning, inductive logic programming, clustering, Bayesian networks, reinforcement learning, representation learning, similarity and metric learning, sparse dictionary learning or genetic algorithms. The processing unit may also comprise a plurality of machine learning components such as for example ANNs wherein each machine learning component is calibrated for extracting a specific object characteristic. For example, a first machine learning component, e.g. ANN, may be trained to detect the type of the object, e.g. a cell. A second machine learning component, e.g. ANN, may be trained to determine the radius of the object, e.g. the cell core. The training or calibration of the machine learning components, e.g. ANNs, is performed by providing them with a large number of labelled training examples first, typically using an algorithm called back-propagation. Such a machine learning component, e.g. an ANN, may be a hardware implemented machine learning component, e.g. ANN. The machine learning component, e.g. ANN, may also be a software routine which is executed by one or more cores, e.g. processors, present on the processing unit. The machine learning component, e.g. ANN, may also be a photonic neural network. In such an embodiment, the processing unit is a photonic circuit which uses light as input instead of electrical signals. As an advantage, phase information of light is not lost because no conversion of the light to electrical signals is done. The optical phase information can be used to increase accuracy of the object identification. Also, the time to identify objects is reduced because the processing unit processes the directly received light. Reference is made to B. Schneider et al., Proc. of SPIE Vol. 9328 93281F-1 which describes an implementation of an ANN in a flow cytometry device, hereby incorporated by reference.

According to an embodiment of the invention, the processing unit may be a hardware implementation of a photonic reservoir computing concept as described in K. Vandoorne et al., Nature Communications, vol. 5, paper 3541, 2014, hereby incorporated by reference. It is an advantage of this embodiment that optical phase information can be used to increase accuracy of the object identification. It is a further advantage of this embodiment that power consumption can be reduced to a minimum as the reservoir processing itself does not consume any power.

According to an embodiment of the invention, the processing unit comprises a multi-processor architecture designed for efficient object characteristic extraction. As an advantage, extraction of different object characteristics may be performed in parallel thereby reducing the total object characterization time.

According to an embodiment of the invention the processing unit comprises a machine learning component being in the present example a support vector machine (SVM) calibrated or trained for extracting at least one object characteristic. The calibration or training of the SVM is similar to the calibration or training of an ANN as described above or other machine learning components.

According to embodiments of the invention, the at least one object characteristic comprises object size and/or object type and/or object internal structure and/or object homogeneity. According to embodiments of the invention, the object is a biological cell. According to embodiments of the invention, the at least one object characteristic comprises a size of the cell and/or a size of a nucleus of the cell and/or cell type and/or cell internal structure and/or cell homogeneity. According to embodiments of the invention, the object is a blood cell, e.g. a red blood cell (RBC) or a white blood cell (WBC) or a circulating tumor cell (CTC).

The device may be placed underneath a sample holder for identifying objects present in the sample holder. The sample holder may be a cavity or a fluidic channel in a substrate, e.g. a silicon substrate. The sample holder may also be a transparent substrate, e.g. a glass substrate.

According to another embodiment of the invention, a device for extracting at least one object characteristic of an object is presented. The device comprises a photonic circuit which is configured for extracting at least one object characteristic from the hologram. The photonic circuit comprises a set of optical in-coupling elements which function as optical inputs to the photonic circuit. The optical in-coupling elements may be grating couplers which are positioned such that a hologram of an illuminated object can be captured. For example, a matrix of optical elements are positioned on a 2D surface such that a complete hologram can be captured. Such a matrix is comparable to a conventional image sensor of which the pixels are replaced by the optical in-coupling elements and wherein the light captured by the in-coupling elements is directly fed to the photonic circuit. The photonic circuit further comprises a photonic processing unit that is optically coupled to the optical in-coupling elements. It is an advantage of the invention that directly captured light is processed by the photonic circuit without conversion to electrical signals. This accelerates the processing and reduces power consumption to a minimum.

According to an embodiment of the invention, the device is a lens-free device. Thus, no lens is present in between the coherent light source and the object and in between the object and the device.

The device may be used in a static setup which comprises a transparent sample holder, a coherent light source for illuminating a fluid sample provided in the sample holder and a device positioned underneath the sample holder for identifying objects in the provided fluid sample after illumination. In such a setup, the fluid sample is not propagating. In this setup a conventional image sensor may be used that records holograms of a plurality of object simultaneously in an image. The processing unit is then configured to detect the different holograms in an image and extract from each hologram a section. These steps may done using simple image processing steps running on the processing unit. The processing unit is then further configured to extract object characteristics from each extracted section.

In a second aspect of the invention, an object sorting system is presented. The system is capable of sorting different types of objects, e.g. cells, present in a fluid sample. The system comprises at least one fluidic channel for propagating a fluid sample comprising objects. The system may comprise a plurality of fluidic channels, e.g. 100 or 1000 channels, for distributing the fluid sample over the different fluidic channels and perform object identification and sorting in parallel. The fluidic channels may be microfluidic channels. The system further comprises at least one coherent light source for illuminating propagating objects. The coherent light source is associated with each fluidic channel such that objects in the fluidic channel can be sufficiently illuminated for lens-free imaging purposes. So, each fluidic channel can be illuminated with a coherent light source or light signal. The coherent light source may be a single coherent light source of which the light signal is distributed over the object sorting system to each fluidic channel. Such distribution can be achieved by using an optical distribution network. With each fluidic channel, an optical out-coupling structure, e.g. a grating coupler, may be associated for coupling a light signal out of the optical distribution network and illuminating that fluidic channel. The system further comprises at least one device as described in the first aspect of the invention. The device is positioned at each fluidic channel such that holograms of objects in the fluidic channel can be captured or recorded as they are illuminated and propagate through the fluidic channel. The device may, for example, form a wall of the fluidic channel. The device may also be positioned underneath a transparent wall of the fluidic channel such that light can be received from illuminated objects. Downstream of the fluidic channel, a sorter is positioned. The sorter may be a micro-fluidic sorter. The sorter is coupled to the fluidic channel, e.g. fluidically coupled, to allow manipulation of the trajectory path of propagating objects in the fluidic channel. Such manipulation may comprise generating microbubbles in that fluidic channel using heating elements. The sorter is also coupled, e.g. electrically, to the device for receiving information from the processing unit. Based on the output of the processing unit, the sorter sorts the objects according to their extracted object characteristics.

Figure 5:
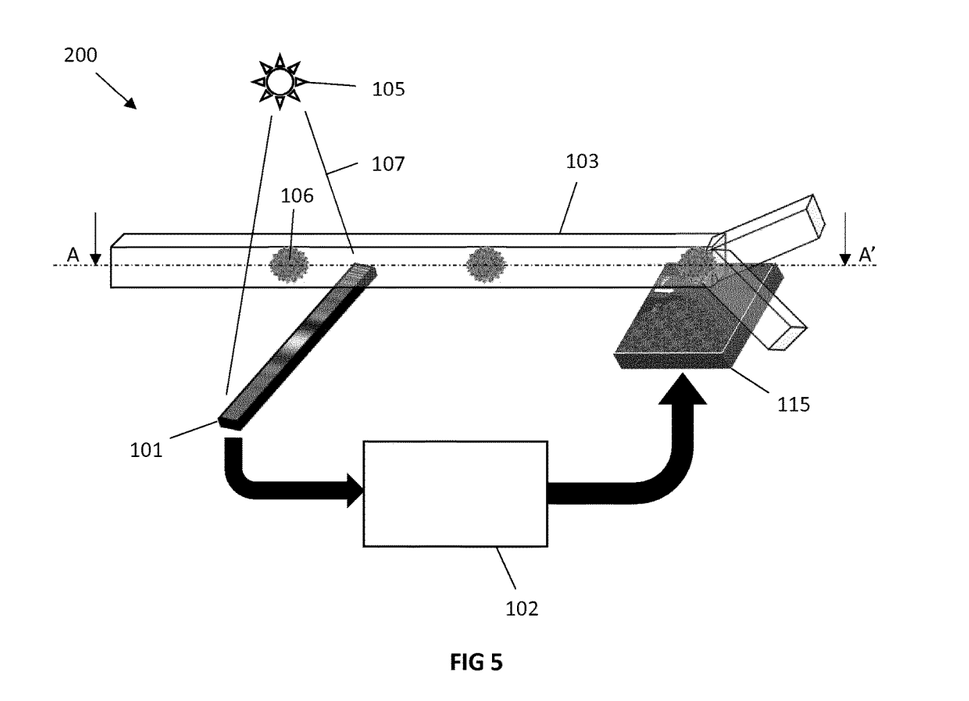
FIG. 5 illustrates an object sorting system according to an embodiment of the present invention.

FIG. 5 illustrates an embodiment of an object sorting system 200. Fluidic channel 103 propagates a fluid sample comprising objects 106. As each object propagates through the channel 103 it passes the light wavefront 107 of the coherent light source 105 and is illuminated. The hologram of the illuminated object is recorded or captured by the light sensor 101. The hologram is transferred to the processing unit 102. After extraction of object characteristics from the hologram, the processing unit 102 instructs the sorter 115 to sort the object as it passes the sorter 105. At the level of the sorter 115, the fluidic channel is split into two other fluidic channels. Depending on the object characteristic, the object is sorted, e.g. deflected, by the sorter 115 to the appropriate other fluidic channel. Depending on the number of different determined object characteristics, the fluidic channel may be split into a plurality of other fluidic channels or wells.

The object sorting system may be a microchip. The microchip may be completely fabricated using semiconductor processing techniques, e.g. CMOS processing step. It is an advantage of the invention that object sorting may be performed completely on-chip. This contributes to the compactness and low cost of the system. Layers of the microchip may, for example, comprise a substrate, e.g. a silicon substrate, the coherent light source(s), the light sensor(s), the fluidic channel(s), the sorter(s) and the processing unit(s).

Figure 6:
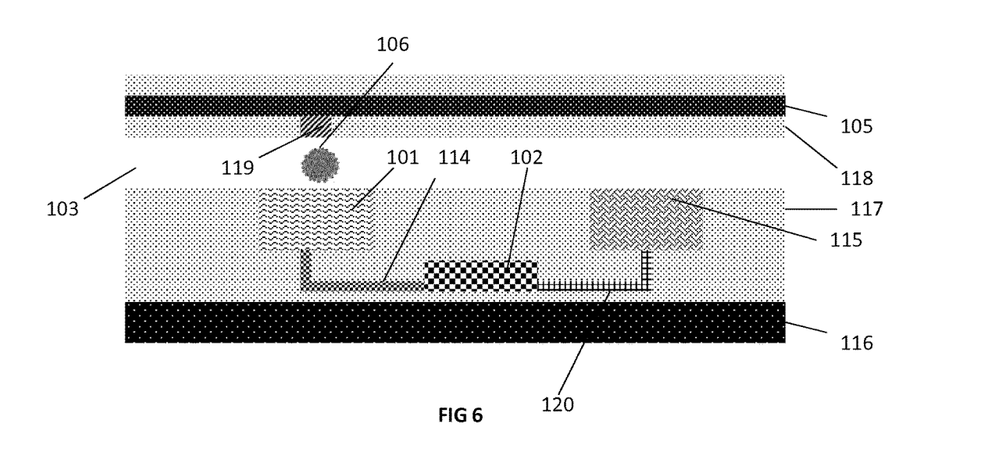
FIG. 6 illustrates a cross section of an object sorting system according to an embodiment of the present invention.

FIG. 6 illustrates an embodiment of cross-section A-A' of FIG. 5. A substrate 116 supports the complete system. This may be a semiconductor substrate, e.g. a silicon substrate. A semiconductor layer 117 is located on top of the substrate 116. This layer 117 may be a semiconductor oxide layer. Embedded in the layer 117 are a light sensor 101, a processing unit 102 and a sorter 115. The layer 117 also comprises couplings 114, 120 which couple the light sensor 101 to the processing unit 102 and the processing unit 102 to the sorter 115, for example, electrically or optically. The light sensor 101, the processing unit 102, the sorter 115 and the couplings 114, 120 between these components may be located in the same layer or in different layers of the microchip, depending on the manufacturing method of the system. Further atop, a fluidic channel 103 is located. On top of the fluidic channel 103, a layer 118 comprising the coherent light source 105 is located. The layer 118 may be a semiconductor layer such as a semiconductor oxide layer. In FIG. 6, the coherent light source 105 is an optical waveguide. The optical waveguide comprises a light outcoupling structure 119, e.g. a grating coupler, located above the light sensor 101 such that an object 106 located in the fluidic channel 103 above the light sensor 101 can be illuminated and its hologram recorded by the light sensor 101. According to an embodiment of the invention, the system comprises a plurality of fluidic channels, wherein each fluidic channel has such a light out-coupling structure associated with it, for illumination of that fluidic channel.

According to a particular embodiment of the invention, the object sorting system is capable of sorting 1 million objects per second. The system comprises 1000 fluidic channels. Each fluidic channel is capable of processing 1000 objects/second. Each fluidic channel comprises a light sensor with 512 pixels (single line of pixels) to record a slice of the holograms of objects propagating through that fluidic channel. The light sensor is capable of recording 25M samples/second. The recorded slices are transferred to a 3 vector products (3 Multiply-Accumulate+Max) SVM which processes each hologram slice in less than 1 millisecond. The SVM is coupled to a sorter which sorts the cells based on the processing results of the SVM.

According to an embodiment of the invention, the object sorting system is a lens-free system.

In a third aspect of the invention, a method for extracting at least one object characteristic is presented. The method comprises the following steps: 1) providing a fluid sample comprising an object; 2) illuminating the object in the fluid sample; 3) recording or capturing a hologram of the illuminated object; 4) extracting at least one characteristic of the object from the recorded hologram. The extraction of the at least one characteristic of the object is performed using only a section of the recorded hologram, without reconstructing an image representation of the object. According to an embodiment of the invention, the recording of the holograms comprises recording intensity and phase of light of the holograms. The extraction of the at least one characteristic of the object is done using the recorded intensity and phase.

The method described in the third aspect of the invention or in any of its embodiments may be implemented by the device described in the first aspect of the invention or in any of its embodiments.

According to an embodiment of the invention, the method for extracting at least one object characteristic is a lens-free method.

Figure 7:
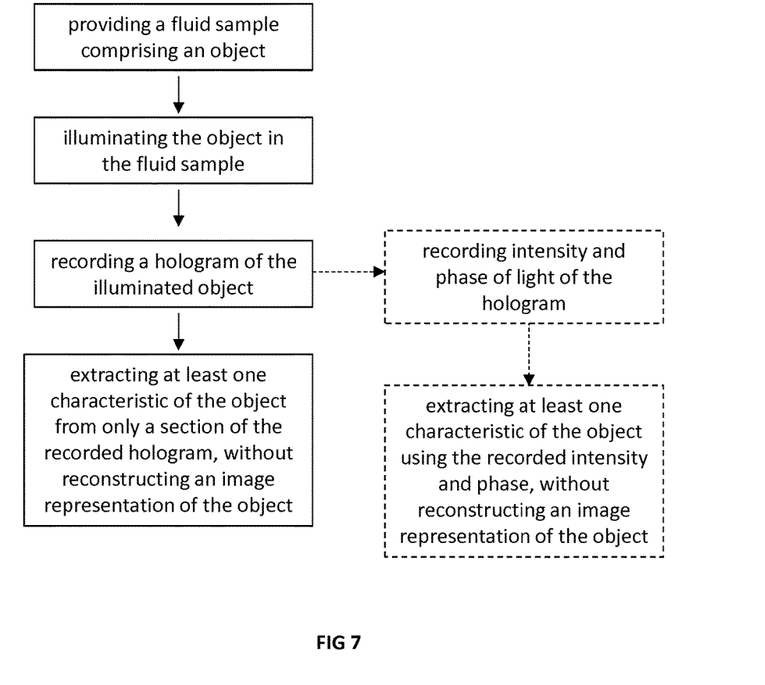
FIG. 7 is a flow chart of a method for identifying an object according to an embodiment of the present invention.

A flow chart of the method according to the third aspect or any of its embodiments is illustrated in FIG. 7.

In a fourth aspect of the invention, the method as described in the third aspect or in any of its embodiments further comprises a step of sorting each object based on the extracted at least one characteristic of that object. Thus, the method is a method for sorting objects.

According to an embodiment of the invention, this method for sorting objects is a lens-free method.

The method described in the fourth aspect of the invention or in any of its embodiments may be implemented by the device described in the second aspect of the invention or in any of its embodiments.

Figure 8:
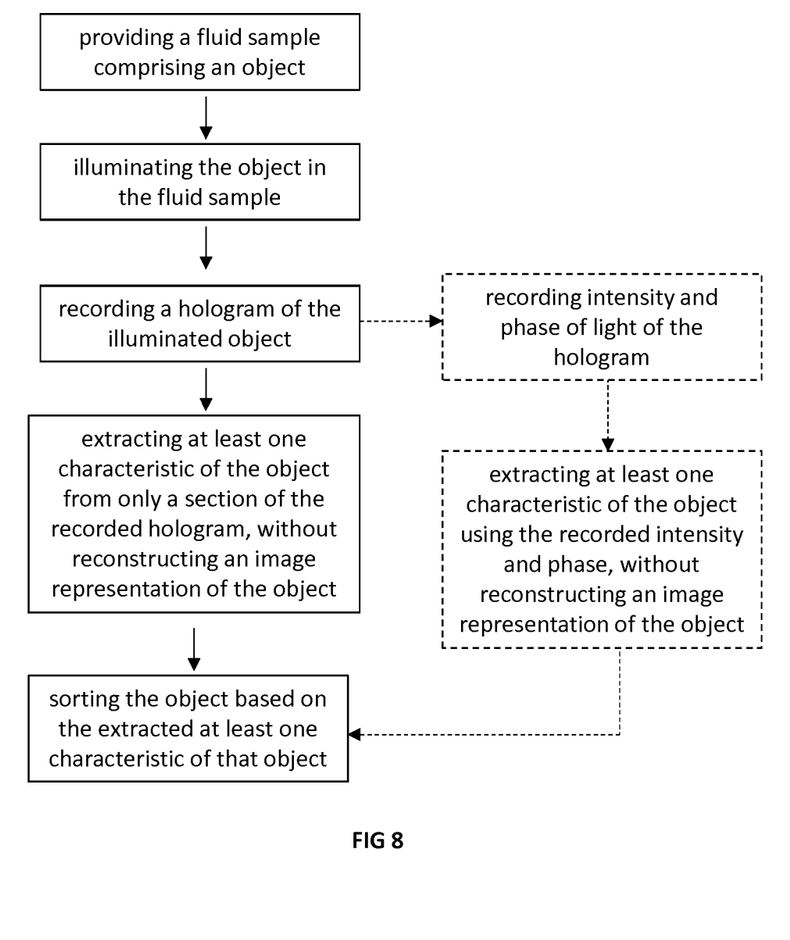
FIG. 8 is a flow chart of a method for sorting an object according to an embodiment of the present invention.

A flow chart of the method according to the fourth aspect or any of its embodiments is illustrated in FIG. 8.

Experiment & Results

In the following paragraphs the setup of an embodiment of the invention comprising an ANN as a machine learning component is described. Also the results are described.

ANNs require a dedicated training set which grows with the number of unknown weights inside the net. To avoid a time-consuming training procedure, the ANN was limit to rather small-size, feed-forward neural nets solely composed of a single hidden layer. The optimal number of hidden neurons is evaluated by cross-validation. For each parameter characterizing the particle a distinct network is trained using a conjugated-gradient based backpropagation algorithm. Early stopping prevents the neural network from overfitting. The neural net is trained with 10 different initial weight distributions so as to eliminate cases where the training algorithm is trapped in a local, non-optimal minimum.

Figure 9:
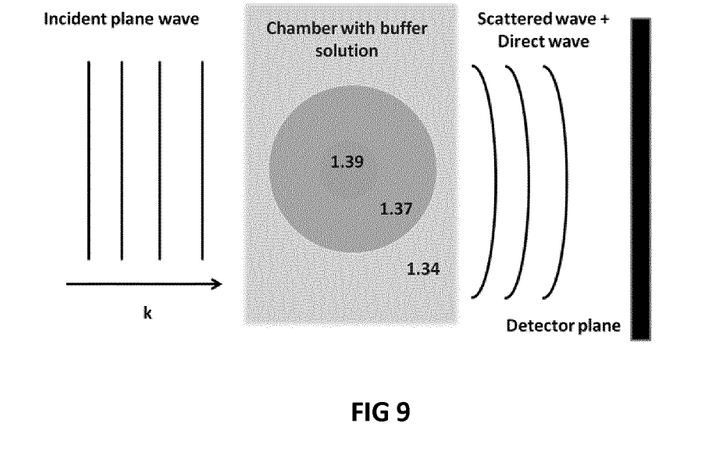
FIG. 9 illustrates a Mie-scattering part using an incident plane wave and an inline image sensor behind the particle which records the hologram, as can be used in an embodiment of the present invention.
Figure 10:
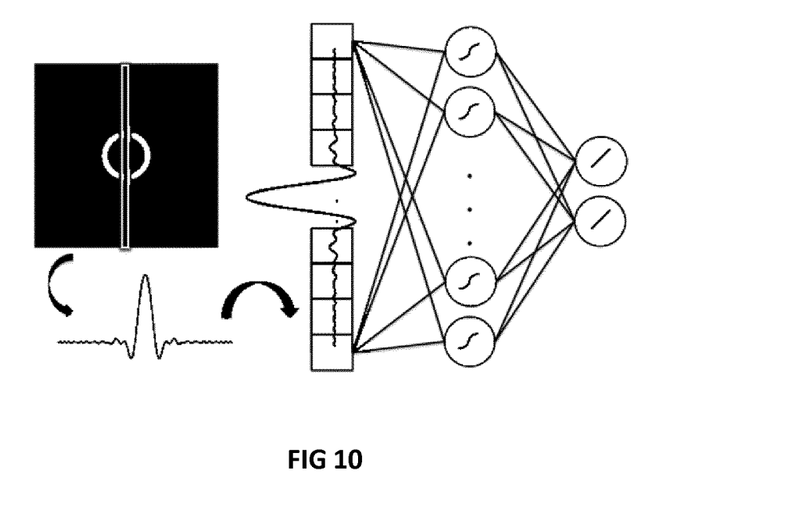
FIG. 10 illustrates the capturing of a radial symmetric hologram and processing by an artificial neural network, as can be used in an embodiment of the present invention.

The training, validation, and test sets consist of random partitions of a catalogue of diffraction patterns. Rigorous Mie-scattering theory is used to calculate the diffraction holograms of concentric spheres at various depths and with different radii under laser illumination. FIG. 9 illustrates the Mie-scattering part using an incident plane wave and an inline image sensor behind the particle which records the hologram. FIG. 10 illustrates a radial symmetric hologram. The underlying symmetry allows one to select only a one-dimensional line scan as input vector to the subsequent neural network. The dimension of the input vector is determined by the number of pixels in one line of the sensor.

Due to the translation and rotation invariance of the diffraction patterns in the detection plane, it is assumed that the particle is located at the origin of the detector's coordinate system and only record the radial dependence. FIG. 10 shows that in this case the hologram is a 512×1 pixel line image recorded by a sensor (pixel pitch 16 um) at 100 um distance which allows for a considerable speed-up of the sensor frame rate in real-time applications.

Figure 11:
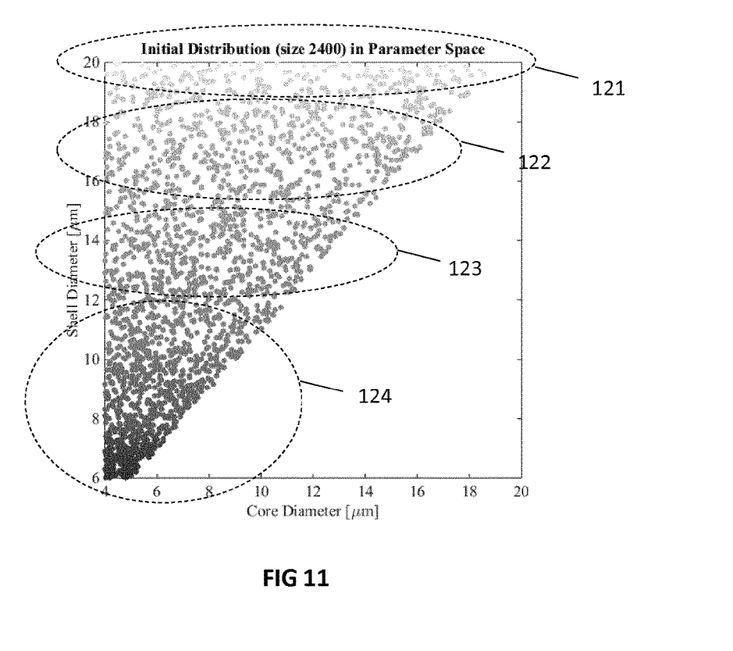
FIG. 11 illustrates the joint distribution of core and shell diameters, as can be used in an embodiment of the present invention.

The Mie scattering patterns of transparent concentric spheres in buffer solution as a simplified model of WBCs are simulated. The following model parameters were chosen: an incident plane wave of wavelength λ=532 nm, a core refractive index (RI) of 1.39, a shell RI of 1.37, and a surrounding medium RI of 1.34. Particle diameters were chosen according to the probability density functions in Eq. 1(a), (b) with a=6 um, b=20 um, and c=4 um. The initial joint distribution of core and shell diameters is shown in FIG. 11. From FIG. 11, different regions 121, 122, 123, 124 can be identified. The depth value of the particles along the optical axis is modeled in terms of a truncated ($|z|\leq 40$ um) Gaussian distribution N(μ=0 um, σ=10 um).

$$p_{core}(x_C) = (b-a)^{-1} 1_{[a,b]} \quad (1a)$$

$$p_{Shell}(x_S|x_C) = (x_C - 1 - c)^{-1} 1_{[c, x_C - 1]}, c < a - 1 \quad (1b)$$

The relative error in diameter sizing is a function of the model parameters. In order to define a global error measure which is defined on the total population, it was proposed the coefficient of variation of the root mean square error (CV) as a normalized error metric. It is defined as the root mean square deviation of the dependent variable y (in this case either the core or shell diameter) divided by the sample mean value.

$$CV = \frac{\sqrt{E[(y - \hat{y})^2]}}{\bar{y}}$$

Another commonly used error measure is the normalized root mean square error (NRMSE). For our settings the NRMSE of the shell diameter is approximately equal to the CV, and the NRMSE of the core diameter is approximately half the CV value. The difference results from the fact that the shell diameter has a uniformly distributed probability density whereas the core diameter has a uniformly distributed conditional probability density.

Figure 12:
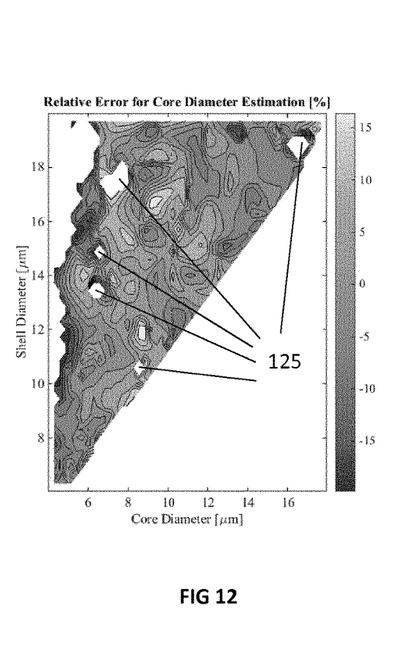
FIG. 12 illustrates the local relative error for each prediction in the test set, as obtained using an embodiment of the present invention.
Figure 13:
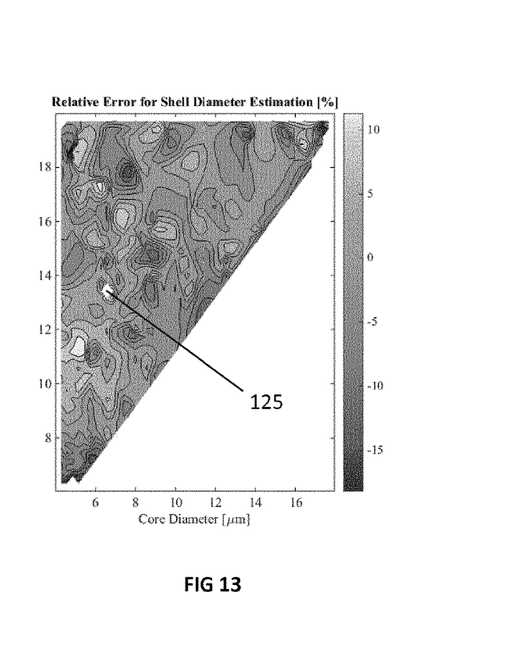
FIG. 13 further illustrates the local relative error for each prediction in the test set, as obtained using an embodiment of the present invention.

The overall prediction accuracy in this error metric is 13% and 7% for the core diameter and shell diameter, respectively. However, much better prediction results are locally achievable. FIG. 12 & FIG. 13 show the local relative error for each prediction in the test set. White spots 125 indicate relative error magnitudes that exceed 20%. No distinctive trend is obvious from the information displayed in the figure except that the core diameter prediction performs poorly for very small core sizes. On the same line the performance decreases typically for similar sized cores and shells. It was demonstrated numerically that characteristic particle parameters can be reliably retrieved by direct investigation of its holographic interference pattern with the help of a single-layered feed-forward neural network. A simple model for light scattering off WBCs was implemented by studying the digital inline holograms of concentric, transparent spheres in the Mie regime. In this sense important cell parameters such as overall cell size and nucleus size can be predicted. Those cell parameters are significant for classification of different groups of WBCs. Our best simulation results for spheres varying between 6 um and 20 um achieve accuracy of 13% and 7% for the core and shell diameter, respectively.

The neural network boosts real-time application because of its intrinsic parallelism and easy to implement matrix operations. All the training experience of the network is stored in its connection weights and hence, no time-consuming look-up procedure in a dictionary-based solution is necessary.

The invention claimed is:

1. A device for extracting at least one characteristic of an object, comprising:
    a light sensor configured for recording at least a section of a hologram of an object, the light sensor consisting of a single row of light recording elements; and
    a processing unit coupled to the light sensor and configured for extracting at least one object characteristic from the hologram,
    wherein the processing unit is configured for extracting the at least one object characteristic from only a section of the hologram without reconstructing an image representation of the object.

2. A device for extracting at least one characteristic of an object, comprising:
    a light sensor configured for recording at least a section of a hologram of an object, the light sensor consisting of two rows of light recording elements intersecting each other thereby forming a cross-shape; and a processing unit coupled to the light sensor and configured for extracting at least one object characteristic from the hologram, wherein the processing unit is configured for extracting the at least one object characteristic from only a section of the hologram without reconstructing an image representation of the object.

3. A device for extracting at least one characteristic of an object, comprising:

a light sensor configured for recording at least a section of a hologram of an object, the light sensor comprising optical in-coupling elements for recording the hologram; and a processing unit coupled to the light sensor and configured for extracting at least one object characteristic from the hologram, wherein the processing unit is configured for extracting the at least one object characteristic from only a section of the hologram without reconstructing an image representation of the object.

4. The device according to claim 1, 2 or 3, wherein the at least one object characteristic comprises at least one of an object size, an object type, an object internal structure, or an object homogeneity.

5. The device according to claim 1, 2 or 3, wherein the object is a biological cell and the at least one object characteristic comprises at least one of a size of the cell, a size of a nucleus of the cell, a cell type, a cell internal structure, or a cell homogeneity.

6. The device according to claim 1, 2 or 3, wherein the object is a red blood cell, a white blood cell, or a circulating tumor cell and the at least one object characteristic comprises at least one of a size of the cell, a size of a nucleus of the cell, a cell type, a cell internal structure, or a cell homogeneity.

7. The device according to claim 1, 2 or 3, wherein the processing unit is a photonic integrated circuit.

8. An in-flow object sorting system, comprising:

at least one fluidic channel for propagating a fluid sample comprising at least one object;

a coherent light source associated with each fluidic channel, positioned to illuminate the object propagating in that fluidic channel;

a device, according to claim 1, 2 or 3, associated with each fluidic channel, positioned to record a section of a hologram of an illuminated object in that fluidic channel; and a sorter associated with each fluidic channel, coupled to the device and positioned downstream of the device, configured for sorting the illuminated object in the associated fluidic channel.

9. A method for extracting at least one characteristic of an object, the method comprising:

providing a fluid sample comprising an object;
illuminating the object;
recording a hologram of the illuminated object;
extracting at least one characteristic of the object from the recorded hologram; and
sorting the object based on the extracted at least one characteristic of the object,
wherein the extraction of the at least one characteristic of the object is performed using only a section of the recorded hologram, without reconstructing an image representation of the object.

10. The method according to claim 9, wherein the recording of the hologram comprises recording intensity and phase of light representing the hologram, and wherein the extraction of the at least one characteristic of the object uses the recorded intensity and the recorded phase of light.

11. The method according to claim 9, wherein the object is a biological cell and the at least one object characteristic comprises at least one of a size of the cell, a size of a nucleus of the cell, a cell type, a cell internal structure, or a cell homogeneity.

12. The device according to claim 1, 2 or 3, wherein the processing unit comprises a machine learning component calibrated for extracting the at least one object characteristic.

13. The device according to claim 12, wherein the machine learning component comprises an artificial neural network or a support vector machine.

14. The device according to claim 1, 2 or 3, wherein recording the hologram and extracting the at least one object characteristic comprises: receiving light of the hologram and determining the at least one object characteristic using the received light without converting the light into electrical signals.

* * * * *